United States Patent
Von Hollen (10) Patent No.: US 10,342,936 B2
(45) Date of Patent: Jul. 9, 2019

(54) SYSTEM AND METHOD FOR MONITORING USAGE OF A RESPIRATORY MEDICATION DELIVERY DEVICE

(71) Applicant: KONINKLIJKE PHILIPS N.V., Eindhoven (NL)

(72) Inventor: Dirk Ernest Von Hollen, Clark, NJ (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 604 days.

(21) Appl. No.: 14/777,944

(22) PCT Filed: Mar. 18, 2014

(86) PCT No.: PCT/IB2014/059915
§ 371 (c)(1),
(2) Date: Sep. 17, 2015

(87) PCT Pub. No.: WO2014/147550
PCT Pub. Date: Sep. 25, 2014

(65) Prior Publication Data
US 2016/0051776 A1  Feb. 25, 2016

Related U.S. Application Data

(60) Provisional application No. 61/803,965, filed on Mar. 21, 2013.

(51) Int. Cl.
*A61M 15/00* (2006.01)
*G06F 19/00* (2018.01)
*A61M 16/00* (2006.01)

(52) U.S. Cl.
CPC ...... *A61M 15/0025* (2014.02); *A61M 15/008* (2014.02); *A61M 15/009* (2013.01);
(Continued)

(58) Field of Classification Search
CPC ......... A61M 15/0025; A61M 16/0003; A61M 15/0026; A61M 15/008
See application file for complete search history.

(56) References Cited

U.S. PATENT DOCUMENTS

| 4,984,158 A * | 1/1991 | Hillsman ............... A61B 5/087 |
| | | 128/200.14 |
| 5,363,842 A | 11/1994 | Mishelevich |

(Continued)

FOREIGN PATENT DOCUMENTS

| JP | 2006305336 A | 11/2006 |
| JP | 2007513647 A | 5/2007 |

(Continued)

*Primary Examiner* — Timothy A Stanis
(74) *Attorney, Agent, or Firm* — Michael W. Haas (57) ABSTRACT

The present disclosure pertains to a system and method for monitoring usage of a respiratory medicament delivery device. Regular use of a respiratory medicament delivery device at intervals prescribed by a doctor may be critical to a subject's health. The system described herein is configured to monitor usage of a respiratory medicament delivery device such that manual tracking of a patient's adherence to a dosage plan by a doctor, for example, is not required. Monitoring usage of the medicament device delivery device may allow the doctor to judge the adherence of the subject to the dosage plan and encourage increased adherence. Improved adherence by the subject may result in improvement in the condition of the subject and economic benefits including reducing costs associated with re-hospitalization after discharge. In some embodiments, the system comprises a medicament delivery device and a usage event monitoring device.

19 Claims, 5 Drawing Sheets

(52) U.S. Cl.
CPC .... *A61M 15/0026* (2014.02); *A61M 16/0003* (2014.02); *G06F 19/3481* (2013.01); *A61M 2016/003* (2013.01); *A61M 2202/064* (2013.01); *A61M 2205/33* (2013.01); *A61M 2205/332* (2013.01); *A61M 2205/3331* (2013.01); *A61M 2205/3368* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/52* (2013.01); *A61M 2205/58* (2013.01); *A61M 2205/82* (2013.01); *A61M 2205/8206* (2013.01); *A61M 2205/8262* (2013.01)

(56) References Cited

U.S. PATENT DOCUMENTS

| | | | |
|---|---|---|---|
| 6,202,642 B1 * | 3/2001 | McKinnon | A61M 15/009 128/200.14 |
| 6,257,231 B1 * | 7/2001 | Shick | A61M 15/0086 128/200.14 |
| 7,040,314 B2 * | 5/2006 | Nguyen | A61K 9/0078 128/200.14 |
| 7,198,172 B2 | 4/2007 | Harvey | |
| 7,495,546 B2 | 2/2009 | Lintell | |
| 8,875,699 B2 | 11/2014 | Bunce | |
| 9,004,062 B2 | 4/2015 | Lang | |
| 2002/0104848 A1 | 8/2002 | Burrows | |
| 2005/0177275 A1 | 8/2005 | Harvey | |
| 2007/0023034 A1 | 2/2007 | Jongejan | |
| 2008/0173301 A1 | 7/2008 | Deaton | |
| 2008/0178872 A1 | 7/2008 | Genova | |
| 2008/0230057 A1 | 9/2008 | Sutherland | |
| 2009/0194104 A1 * | 8/2009 | Van Sickle | A61M 15/00 128/203.12 |
| 2011/0226242 A1 * | 9/2011 | Von Hollen | A61M 15/009 128/203.12 |

FOREIGN PATENT DOCUMENTS

| | | |
|---|---|---|
| JP | 2009542382 A | 12/2009 |
| JP | 2010502388 A | 1/2010 |
| RU | 2336906 C2 | 10/2008 |
| WO | WO0315838 A2 | 2/2003 |
| WO | WO2005020023 A2 | 3/2005 |
| WO | WO2011083377 A1 | 7/2011 |

* cited by examiner

SYSTEM AND METHOD FOR MONITORING USAGE OF A RESPIRATORY MEDICATION DELIVERY DEVICE

CROSS-REFERENCE TO RELATED APPLICATIONS

This patent application claims the priority benefit under 35 U.S.C. § 371 of international patent application no. PCT/IB2014/059915, filed Mar. 18, 2014, which claims the priority benefit under 35 U.S.C. § 119(e) of U.S. Provisional Application No. 61/803,965, filed on Mar. 21, 2013, the contents of which are herein incorporated by reference.

BACKGROUND

1. Field

The present disclosure pertains to a system and method for monitoring usage of a respiratory medicament delivery device.

2. Description of the Related Art

It is well known to deliver a medication to a patient's respiratory system to treat a medical condition using a respiratory drug delivery apparatus. For example, a patient suffering from an acute asthmatic attack may use a respiratory drug delivery apparatus to deliver a bronchodilator, such as albuterol (salbutamol), in the form of a fine mist to the patient's respiratory system. Various drug formulations are available to treat chronic diseases such as asthma and COPD. Patients are routinely prescribed a combination of drugs which may require the use of drug delivery devices such as a pressurized metered dose inhaler (pMDI) or a dry powder inhaler (DPI). Most systems do not include a mechanism to track patient adherence to a dosage routine. Caregivers commonly rely on a patient's oral communication to the caregiver and/or a prescription refill history to assess patient adherence to their dosage routine as prescribed by their physician. Only a few systems are available that include a mechanism to confirm that patients are actually adhering to their routine as prescribed by their physician. Each of these systems sense the pressure exerted by a user on the inhaler during actuation of the inhaler or flow of the medication to track patient use. This requires the system to remain active (powered on), thus increasing power consumption.

SUMMARY

Accordingly, one or more aspects of the present disclosure relate to a system configured to monitor usage of a respiratory medicament delivery device. The medicament delivery device is configured to deliver medicament to an airway of a subject. The medicament delivery device comprises an opening through which medicament is delivered to the subject and a cover configured to be removably installed at the opening in the medicament delivery device to cover the opening. The system comprises a power supply, a processor, and a switch. The switch is configured to selectively connect and disconnect the power supply with the processor such that, responsive to the cover being removed from the opening, the switch connects the power supply with the processor to power up the processor. The processor is configured such that responsive to a power up, the processor causes information related to the power up to be recorded to non-transient electronic storage media.

Yet another aspect of the present disclosure relates a method to monitor usage of a respiratory medicament delivery device with a monitoring system. The medicament delivery device is configured to deliver medicament to an airway of a subject. The medicament delivery device comprises an opening through which medicament is delivered to the subject and a cover configured to be removably installed at the opening in the medicament delivery device to cover the opening. The system comprises a power supply, a processor, and a switch. The method comprises selectively connecting and disconnecting the power supply to the processor with the switch such that, responsive to the cover being removed from the opening, the power supply is connected with the processor by the switch to power up the processor; and responsive to a power up, causing information related to the power up to be recorded to non-transient electronic storage media, the causing performed by the processor.

Still another aspect of the present disclosure relates to a system configured to monitor usage of means for delivering medicament to an airway of a subject. The means for delivering comprising an opening through which medicament is delivered to the subject and a cover configured to be removably installed at the opening in the means for delivering to cover the opening. The system comprising means for powering the system, means for controlling the system, and means for selectively connecting and disconnecting the means for powering with the means for controlling. The means for selectively connecting and disconnecting the means for powering with the means for controlling is configured such that, responsive to cover being removed from the opening, the means for selectively connecting connects the means for powering with the means for controlling to power up the means for controlling. The means for controlling is configured to, responsive to a power up, record information related to the power up to means for non-transient electronic storage.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
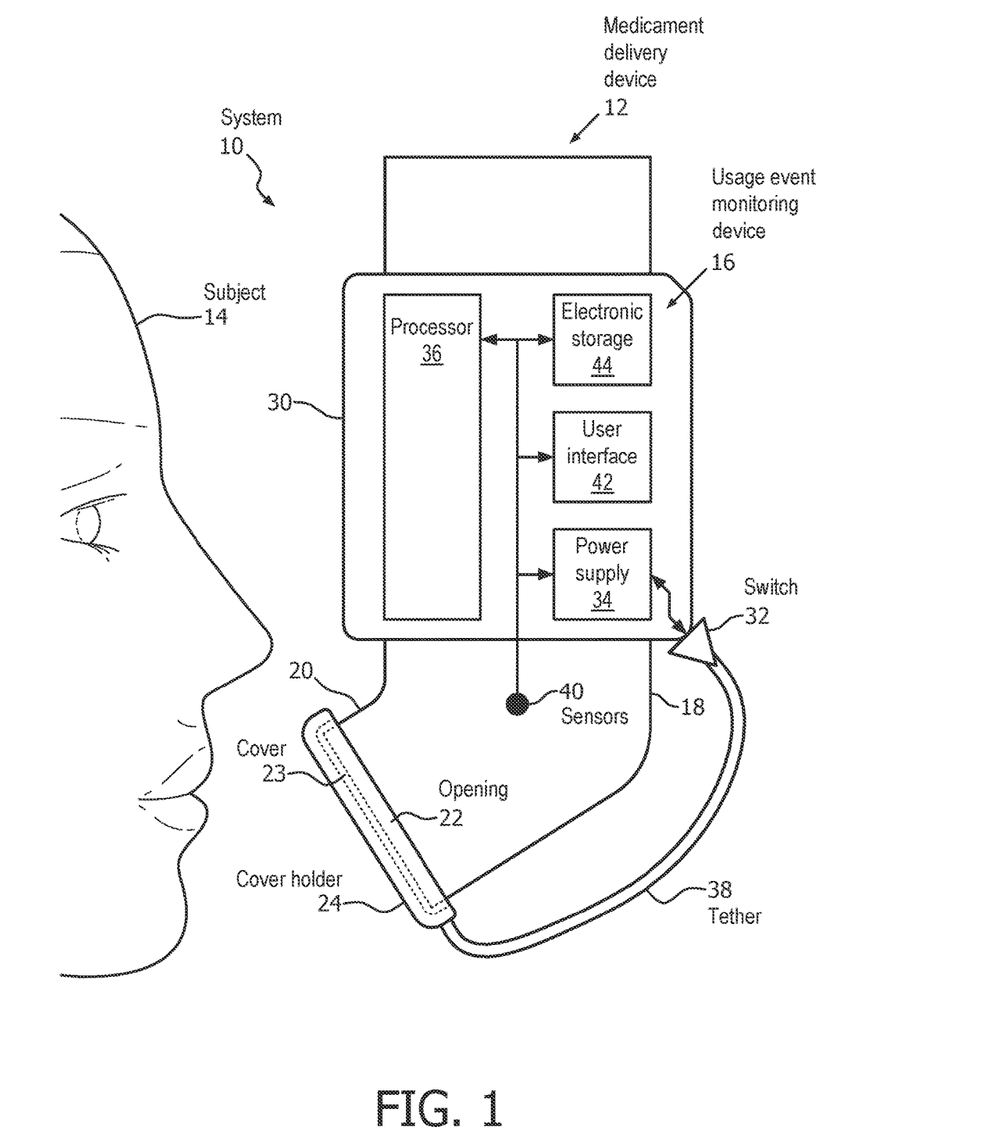
FIG. 1 is a is a schematic illustration of an example embodiment of a system configured to monitor usage of a respiratory medicament delivery device by a subject.

FIG. 1 is a schematic illustration of an example embodiment of a system 10 configured to monitor usage of a respiratory medicament delivery device 12 by a subject 14. Regular use of a respiratory medicament delivery device (e.g., medicament delivery device 12) at intervals is often prescribed by a doctor. System 10 described herein is configured to monitor usage of a respiratory medicament delivery device such that manual tracking of a patient's adherence to a dosage plan by a doctor and/or a patient, for example, is not required. Monitoring usage of medicament delivery device 12 may allow a doctor, for example, to judge the adherence of subject 14 to the dosage plan and encourage increased adherence. Improved adherence by subject 14 may result in improvement in the condition of subject 14 and economic benefits including reducing costs associated with re-hospitalization after discharge, and reducing health events requiring emergency care through early detection and intervention. In some embodiments, system 10 comprises medicament delivery device 12 and a usage event monitoring device 16.

Medicament delivery device 12 is configured to deliver medicament to an airway of a subject 14. Medicament delivery device 12 is configured to aerosolize the medicament for dispensation to subject 14 so that subject 14 may inhale the medicament into his airway. In some embodiments, medicament delivery device 12 may comprise one or more of a metered dose inhaler (MDI), a pressurized metered dose inhaler (pMDI), a dry powder inhaler (DPI), and/or another medicament delivery device. In some embodiments, medicament delivery device 12 may be commonly known as an "inhaler". In some embodiments, medicament delivery device 12 may include a canister, a liquid container, and/or a means to dispense dry medication via an individual or bulk package configuration. Medicament delivery device 12 may be configured to contain the medication under pressure. Medicament delivery device 12 may include a canister holder, commonly called a boot 18, so named because the canister holder is roughly boot shaped. In some embodiments, boot 18 is configured such that subject 14 may use an end 20 of boot 18 as a mouthpiece for receiving the aerosolized medication into the airway of subject 14. The aerosolized medication may be received directly from the aerosol dispensing leg of boot 18 through an opening 22. Opening 22 is configured such that medicament is delivered to the airway of subject 14 through opening 22. A cover 23 is configured to be removably installed at opening 22 of medicament delivery device 12 to cover opening 22. In some embodiments, end 20 and/or opening 22 are configured to be non-invasively engaged by the mouth of subject 14. Non-invasive engagement comprises removably engaging one or more external orifices of the airway of subject 14 (e.g., mouth) to communicate gas between the airway of subject 14 and medicament delivery device 12. In some embodiments, medicament delivery device 12 may be removably engaged with an accessory such as a valved holding chamber.

Usage event monitoring device 16 is configured to detect and record medicament delivery device usage events. Usage event monitoring device 16 may be configured to monitor one or more aspects of the dispensation of medicament from medicament delivery device 12. In some embodiments, usage event monitoring device 16 comprises a cover holder 24, a switch 32, a power supply 34, a processor 36, a tether 38, one or more sensors 40, a user interface 42, electronic storage 44, and/or other components. Medicament delivery device usage events may include one or more of removing cover 23 from opening 22 of medicament delivery device 12, powering up usage event monitoring device 16, dispensing medication from medicament delivery device 12, and/or other medicament delivery device usage events. Cover holder 24 is configured to be removably coupled to cover 23 of medicament delivery device 12 such that responsive to cover 23 being removed from opening 22, cover 23 remains coupled with cover holder 24. In some embodiments, cover holder 24 may be configured to be removably installed directly on opening 22 (e.g., without cover 23) of medicament delivery device 12 to cover opening 22.

Usage event monitoring device 16 is configured to be removably coupled to medicament delivery device 12 such that medicament delivery device 12 need not be altered to accommodate usage event monitoring device 16. Usage event monitoring device 16 may be removably coupled to medicament delivery device 12 by a housing 30 of usage event monitoring device 16. Housing 30 is configured to contain switch 32, power supply 34, processor 36, user interface 42, electronic storage 44, and/or other components of usage event monitoring device 16. Housing 30 is configured to contain the components of usage event monitoring device 16 in a space small enough such that system 10 may be handheld and portable so therapy may be delivered at any time during the normal daily activities of subject 14. In some embodiments, usage event monitoring device 16 may be removably coupled to medicament delivery device 12 by friction, a mechanical coupling mechanism, an adhesive, and/or other removable coupling methods. Removably coupling usage event monitoring device 16 to medicament delivery device 12 may facilitate easier cleaning of system 10, transferring usage event monitoring device 16 to another inhaler, and/or other activities. In some embodiments, usage event monitoring device 16 may be incorporated as part of medicament delivery device 12 in a one piece assembly.

Switch 32 is configured to selectively connect and disconnect power supply 34 with one or more of processor 36, sensors 40, user interface 42, electronic storage 44, and/or other components of usage event monitoring device 16. Switch 32 is configured to connect power supply 34 to one or more of processor 36, sensors 40, user interface 42, electronic storage 44, and/or other components of usage event monitoring device 16 responsive to cover 23 and/or cover holder 24 being removed from opening 22. Switch 32 connects power supply 34 with processor 36, sensors 40, user interface 42, electronic storage 44, and/or other components of usage event monitoring device 16 to power up processor 36, sensors 40, user interface 42, electronic storage 44, and/or other components of usage event monitoring device 16. In some embodiments, switch 32 is an electrical component configured to interrupt an electrical circuit to disrupt the flow of an electrical current between power supply 34 and one or more of processor 36, sensors 40, user interface 42, electronic storage 44, and/or other components of usage event monitoring device 16. Examples of switch 32 may include a tactile switch, an electromechanical switch, a biased switch, a toggle switch, a trembler switch, a limit switch, a knife switch, an optical sensor based switch, an acoustic sensor based switch (e.g., an acoustic sensor based switch may connect power supply 34 to one or more other components of usage event monitoring device 16 bases on the sound of cover 23 and/or cover holder 24 being removed from opening 22), and/or other switches.

Power supply 34 is configured to power processor 36, sensors 40, user interface 42, electronic storage 44, and/or other components of system 10 in a portable manner. Power supply 34 may comprise one or more power sources connected in series and/or in parallel. In some embodiments, power supply 34 is rechargeable. Power supply 34 may be recharged via a home AC power source, a car battery outlet, an airplane power outlet, a USB port, a non-contact charging circuit, and/or other recharging methods.

Processor 36 is configured to cause information related to a power up to be recorded to non-transient electronic storage media. Processor 36 is configured such that responsive to the power up, the processor causes information related to the power up to be recorded to electronic storage 44. Information related to the power up may include a date, a time of day, inhaler type, and/or other information. In some embodiments, processor 36 may be configured to cause storage of information related to use of medicament delivery device 12 during one or more treatment sessions. A treatment session may include use of medicament delivery device 12 over the time period between removal of cover 23 and/or cover holder 24 from opening 22 until replacement of cover 23 and/or cover holder 24 on opening 22. Such stored information may include the timing of an inhalation from medicament delivery device 12 (e.g. frequency of inhalations), the length of an inhalation, the length of time the inhaler was shaken prior to inhalation, the length of time between shaking and actuation of the inhaler, and/or other information. In some embodiments, processor 36 may be configured to cause storage of information related to the output signals generated by sensors 40.

Processor 36 is configured to provide information processing capabilities in system 10. As such, processor 36 may comprise one or more of a digital processor, an analog processor, a digital circuit designed to process information, an analog circuit designed to process information, a state machine, and/or other mechanisms for electronically processing information. Although processor 36 is shown in FIG. 1 as a single entity, this is for illustrative purposes only. In some embodiments, processor 36 may comprise a plurality of processing units. These processing units may be physically located within the same device (e.g., usage event monitoring device 16), or processor 36 may represent processing functionality of a plurality of devices operating in coordination.

In some embodiments, processor 36 may be configured to communicate information related to a power up, information related to the use of medicament delivery device 12, and/or other information to a heath care provider, for example. Processor 36 may be configured to communicate the information wirelessly over a network (e.g., the internet). In some embodiments, processor 36 may be configured to receive information wirelessly over a network and display the information to subject 14 via user interface 42. By way of a non-limiting example, processor 36 may receive information related to a treatment reminder sent by a doctor.

Tether 38 is configured to actuate switch 32 responsive to cover 23 and/or cover holder 24 being removed from opening 22 in medicament delivery device 12. Actuation of switch 32 comprises changing the state of switch 32 from a state in which the flow of electrical current from power supply 34 is interrupted to a state in which electrical current may flow from power supply 34 to the other components of usage event monitoring device 16. In some embodiments, tether 38 may be attached to cover holder 24 such that cover holder 24 remains attached to tether 38 when cover 23 and/or cover holder 24 are removed from opening 22. In some embodiments, tether 38 may be removably coupled to cover holder 24. In some embodiments, tether 38 may be attached directly to cover 23. In some embodiments, tether 38 may be removably coupled to cover 23. The approximate shape and location of tether 38 shown in FIG. 1 are not intended to be limiting. Tether 38 may take any shape, be formed from any material, and reside in any location such that tether 38 functions as described herein.

One or more sensors 40 are configured to generate output signals conveying information related to one or more of parameters of the flow of medicament in system 10, and/or parameters related to monitoring patient usage activity of system 10. Sensors 40 may include accelerometers, temperatures sensors, flow sensors, acoustic sensor, and/or other sensors. Sensors 40 are configured to be powered by power supply 34 responsive to switch 32 connecting power supply 34 to sensors 40 (switch 32 connecting power supply 34 to sensors 40 responsive to cover 23 and/or cover holder 24 being removed from opening 22). In some embodiments, processor 36 is configured to cause information related to the one or more parameters of the flow of medicament and/or the parameters related to monitoring patient usage activity of system 10 to be recorded to non-transient electronic storage media 44.

The one or more parameters of the flow of medicament within system 10 may comprise gas parameters related to the aerosolized flow of medicament, and/or other parameters. Sensors 40 may comprise one or more sensors that measure such parameters directly (e.g., a flow sensor and/or a temperature sensor in fluid communication with the flow of medicament in boot 18). Sensors 40 may comprise one or more sensors that generate output signals related to the one or more parameters indirectly. For example, sensors 18 may comprise one or more acoustic sensors configured to generate an output based on sound waves generated during use of system 10, and/or other sensors.

The one or more parameters of the flow of medicament may comprise, for example, one or more of a flow rate, a volume, a pressure, humidity, temperature, acceleration, velocity, composition, a timing (e.g., beginning and/or end of inhalation, beginning and/or end of exhalation, etc.), a usage frequency, and/or other parameters. The one or more parameters related to monitoring patient usage activity of system 10 may include parameters related to a subject 14 loading a dry powder capsule into system 10 (e.g., frequency, date, time), the lung function of subject 14, the breathing technique of subject 14, and/or other parameters.

Although sensors 40 are illustrated in FIG. 1 at a single location in system 10, this is not intended to be limiting. Sensors 40 may comprise sensors disposed in a plurality of locations, such as for example, at various locations within (or in communication with) boot 18, within (or in communication with) opening 22, and/or other locations.

User interface 42 is configured to provide an interface between system 10 and subject 14 and/or other users through which subject 14 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 14) and processor 36, electronic storage 44, and/or other components of system 10. For example, a user may define a time period and view the dates and times system 10 was used by subject 14 during that time period using user interface 42. In some embodiments, a doctor and/or other care giver make treatment decisions based on information viewed via user interface 42.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 42 comprises a plurality of separate interfaces. In one embodiment, user interface 42 comprises at least one interface that is provided integrally with housing 30.

It is to be understood that other communication techniques, either hard-wired or wireless, are also contemplated by the present disclosure as user interface 42. For example, the present disclosure contemplates that user interface 42 may be integrated with a removable storage interface provided by electronic storage 44. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 42 comprise, but are not limited to, an RS-232 port, RF link, an IR link, modem (telephone, cable or other). In short, any technique for communicating information with system 10 is contemplated by the present disclosure as user interface 42.

In some embodiments, non-transient electronic storage 44 comprises electronic storage media that electronically stores information. The electronic storage media of electronic storage 44 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 44 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 44 may store software algorithms, information determined by processor 36, information received via user interface 42, and/or other information that enables system 10 to function properly. Electronic storage 44 may be (in whole or in part) a separate component within system 10, or electronic storage 44 may be provided (in whole or in part) integrally with one or more other components of system 10 (e.g., user interface 42, processor 36, etc.).

Information determined by processor 36 and/or stored by electronic storage 44 may comprise information related to a power up of usage event monitoring device 16, use frequency and/or other information related to medicament delivery device 12, and/or other information. The information stored by electronic storage 44 may be viewed via user interface 42, by connecting (wired and/or wireless) to a separate computer, and/or other via other methods. The information stored by electronic storage 44 may be used, for example, to adjust medicament delivery device 12, to make adjustments to power supply 34, used by a doctor to make medical decisions, and/or for other uses.

Figure 2:
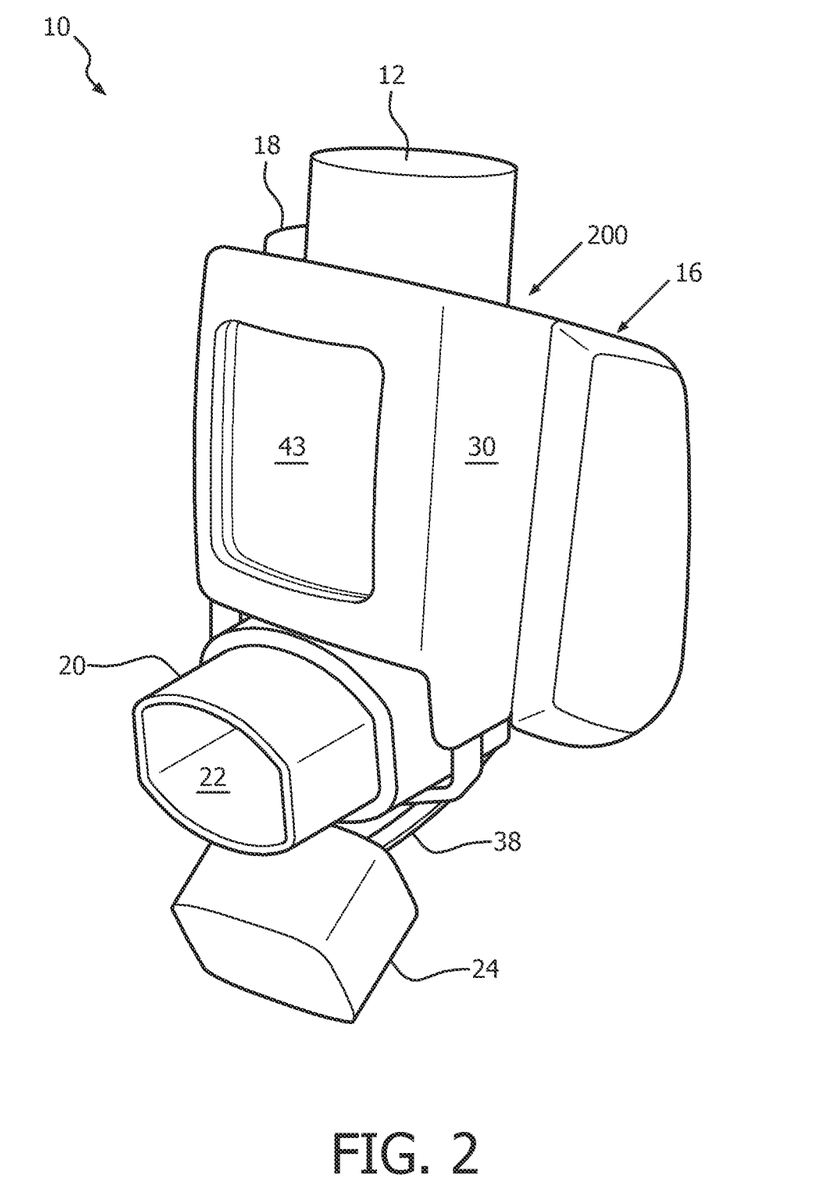
FIG. 2 is a perspective view of the example embodiment of a system configured to monitor usage of a respiratory medicament delivery device by a user.

FIG. 2 is a perspective view of the example embodiment of system 10 schematically illustrated in FIG. 1. In FIG. 2, cover 23 (not shown in FIG. 2) and cover holder 24 have been removed from opening 22 at end 20 of boot 18 in medicament delivery device 12. In FIG. 2, viewing port 43 is provided integrally with housing 30 such that a user may view pMDI (for example) labeling that is typically embossed on boot 18. In some embodiments, housing 30 is made of a rigid material such as a hard plastic or some other suitable rigid material. In some embodiments, housing 30 may be a single rigid plastic housing. In some embodiments, housing 30 may comprising a flexible material coupled to a rigid housing. Housing 30 includes a recess 200 that is configured to receive boot 18 of medicament delivery device 12. The arrangement of housing 30 and boot 18 shown in FIG. 2 is not intended to be limiting. Boot 18 and housing 30 may be configured with any arrangement that allows system 10 to function as described herein (e.g., the positioning arrangement of housing 30 and boot 18 does not interfere with the dispensing of medicament from medicament delivery device 12, usage event monitoring device 16 is removably coupled to medicament delivery device 12, power supply 34 (not shown in FIG. 2) powers usage event monitoring device 16 responsive to cover 23 and/or cover holder 24 uncovering opening 22, etc.).

Figure 3:
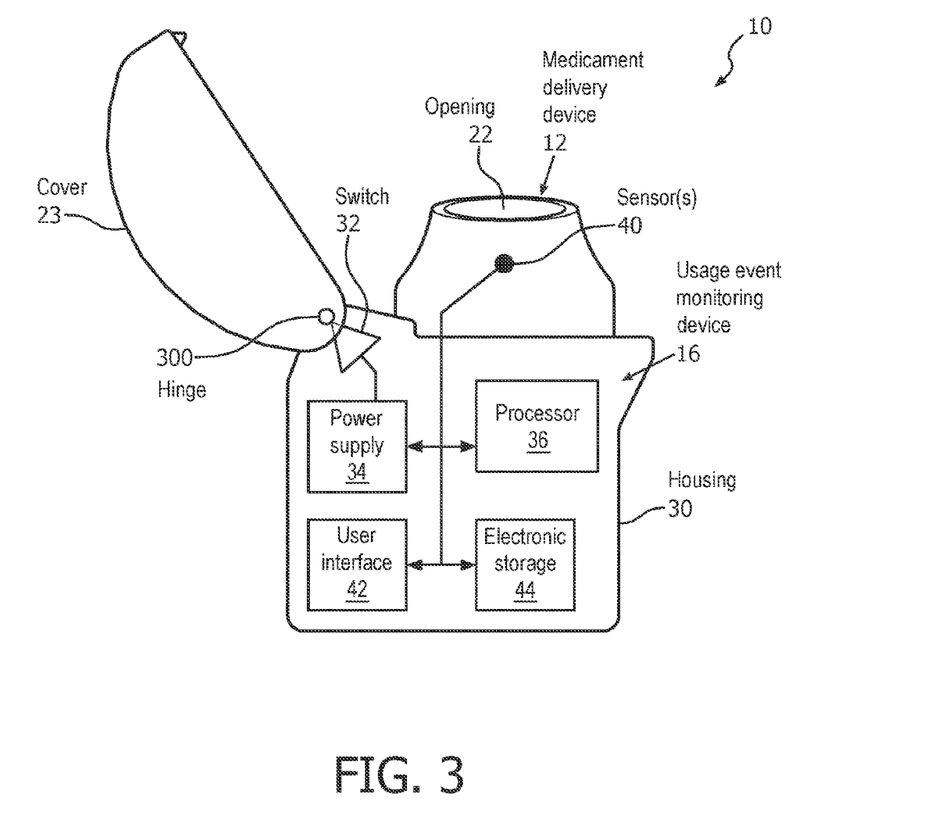
FIG. 3 is a schematic illustration of a second example embodiment of a system configured to monitor usage of a respiratory medicament delivery device by a subject.

FIG. 3 is a schematic illustration of a second example embodiment of system 10. As such, the descriptions of the components in the first embodiment of system 10 described above apply to the corresponding components of system 10 shown in FIG. 3. In the embodiment of system 10 shown in FIG. 3, cover 23 may be coupled to housing 30 by way of a hinge 300. Cover 23 covers and/or uncovers opening 22 responsive to pivoting at hinge 300. In some embodiments, switch 32 may be coupled to hinge 300, to cover 23 and/or to another component of system 10. Switch 32 may be actuated by hinge 300, actuated directly by cover 23, and/or actuated by another mechanism.

Figure 4:
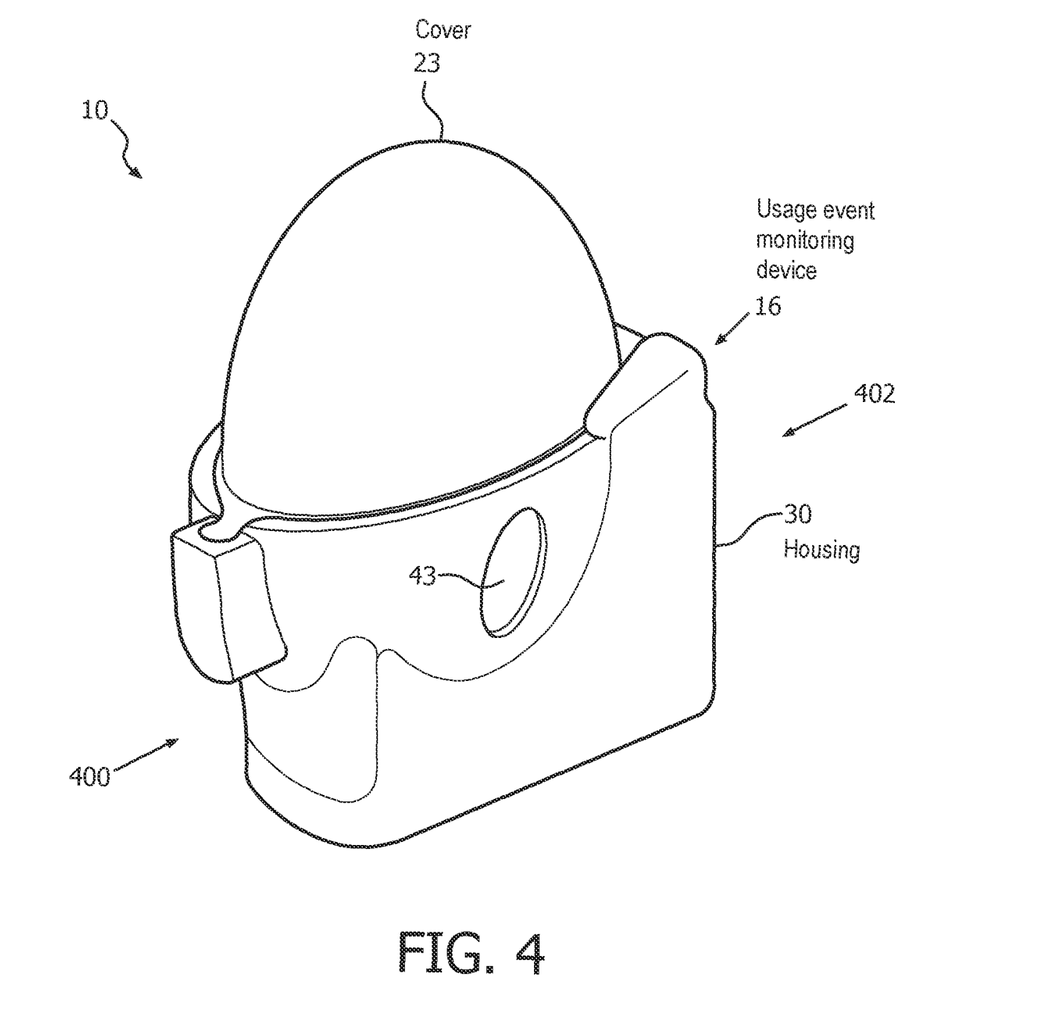
FIG. 4 is a perspective view of the second example embodiment of a system configured to monitor usage of a respiratory medicament delivery device by a subject.

FIG. 4 is a perspective view of the example embodiment of system 10 schematically illustrated in FIG. 3. In FIG. 4, cover 23 is shown covering opening 22 (not visible in FIG. 4). In some embodiments, (not shown in FIG. 4) cover 23 may be configured to cover and/or uncover opening 22 by sliding toward an end 400, 402 of usage event monitoring device 16.

Figure 5:
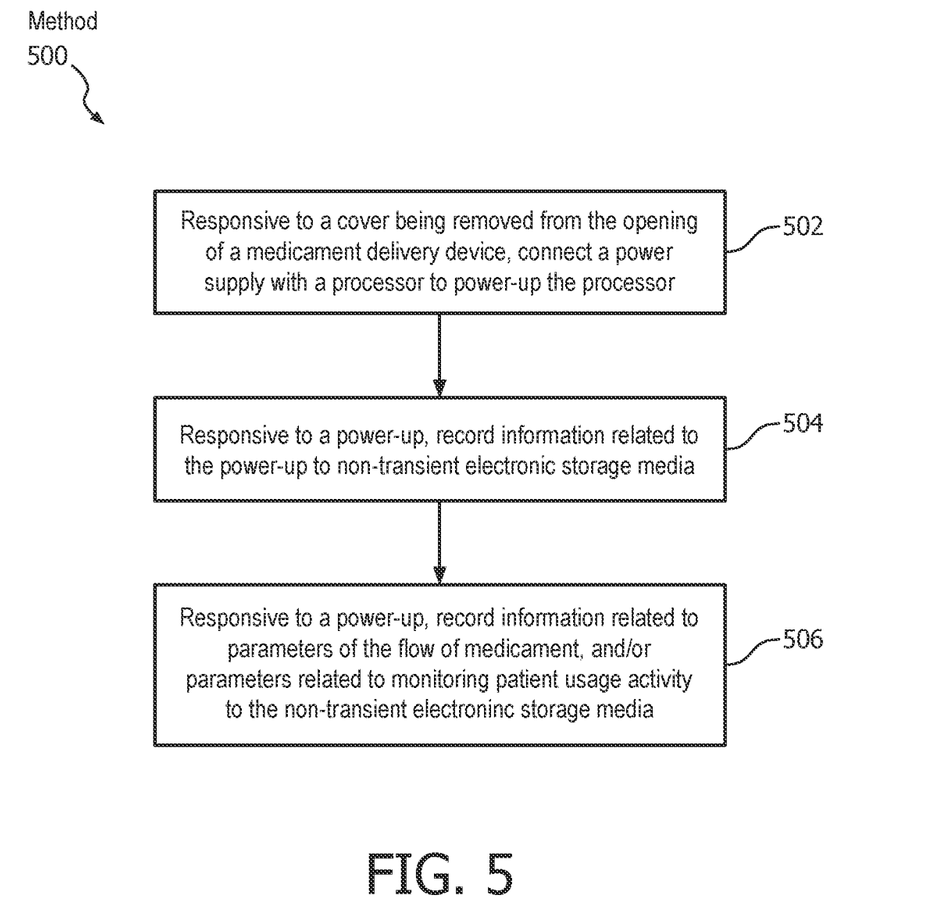
FIG. 5 is an illustration of a method to monitor usage of a respiratory medicament delivery device by a subject.

FIG. 5 illustrates a method 500 for monitoring usage of a respiratory medicament delivery device with a monitoring system. The medicament delivery device is configured to deliver medicament to an airway of a subject. The medicament delivery device comprises an opening through which medicament is delivered to the subject and a cover configured to be removably installed at the opening in the medicament delivery device to cover the opening. The system comprises a power supply, a processor, and a switch. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, responsive to the cover being removed from the opening of the medicament delivery device, the power supply is connected with the processor to power up the processor. The connecting is performed by the switch. In some embodiments, operation 502 is performed by a switch the same as or similar to switch 36 (shown in FIG. 1 and described herein.)

At an operation 504, responsive to a power up, information related to the power up is recorded to the non-transient electronic storage media. In some embodiments, operation 504 is performed by a processor the same as or similar to processor 34 (shown in FIG. 1 and described herein.)

At an operation 506, responsive to a power up, information related to parameters of the flow of medicament, and/or parameters related to monitoring patient usage activity are recorded to the non-transient electronic storage media. In some embodiments, operation 506 is performed by a processor the same as or similar to processor 34 (shown in FIG. 1 and described herein.) In some embodiments, the information related to the parameters of the flow of medicament and/or the parameters related to monitoring patient usage activity may be related to the output signals generated by sensors 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to monitor usage of a respiratory medicament delivery device, the medicament delivery device configured to deliver medicament to an airway of a subject, the medicament delivery device comprising an opening through which medicament is delivered to the subject, the system comprising:
   a cover configured to cover the opening;
   a power supply;
   a processor; and
   a switch configured to selectively connect and disconnect the power supply with the processor such that, responsive to the cover being removed from the opening, the switch connects the power supply with the processor to power up the processor, the cover being releasably connected with the switch and remains connected to the switch even when the cover is disengaged from the opening, and wherein the processor is configured such that responsive to a power up, the processor causes information related to the power up to be recorded to non-transient electronic storage media, wherein the information related to the power up includes a date and time of the power up.

2. The system of claim 1, further comprising a cover holder configured to removably couple to the cover, wherein the cover holder is connected to the switch by way of a tether, and wherein the tether is configured to actuate the switch responsive to the cover being removed from the opening in the medicament delivery device.

3. The system of claim 1, further comprising one or more sensors configured to generate one or more output signals conveying one or more of information related to one or more parameters of a flow of medicament from the medicament delivery device to the subject, or information related to one or more parameters indicative of usage activity between the subject and the medicament delivery device, wherein the one or more sensors are powered by the power supply responsive to the switch connecting the power supply to the one or more sensors, the switch connecting the power supply to the one or more sensors responsive to the cover being removed from the opening in the medicament delivery device, and wherein the processor is configured to cause information related to one or more of the one or more parameters of the flow of medicament, or the one or more parameters indicative of usage activity between the subject and the medicament delivery device to be recorded to the non-transient electronic storage media.

4. The system of claim 1, wherein the system is removably coupled to the medicament delivery device such that the medicament delivery device need not be altered to accommodate the system.

5. The system of claim 1, wherein the medicament delivery device is one or more of a metered dose inhaler, a pressurized metered dose inhaler, or a dry powder inhaler.

6. The system of claim 1, wherein the information related to the power up further includes a type of the respiratory medicament delivery device.

7. The system of claim 1, wherein the cover is releasably connected to the switch via a tether.

8. A method to monitor usage of a respiratory medicament delivery device with a monitoring system, the medicament delivery device configured to deliver medicament to an airway of a subject, the medicament delivery device comprising an opening through which medicament is delivered to the subject and a cover configured to cover the opening, the monitoring system comprising a power supply, a processor, and a switch, the method comprising:

selectively connecting and disconnecting the power supply to the processor with the switch such that, responsive to the cover being removed from the opening, the power supply is connected with the processor by the switch to power up the processor, wherein the cover is releasably connected with the switch and remains connected to the switch even when the cover is disengaged from the opening; and responsive to a power up, causing information related to the power up to be recorded to non-transient electronic storage media, the causing performed by the processor, wherein the information related to the power up includes a date and time of the power up.

9. The method of claim 8, further comprising tethering the cover to the switch with a cover holder and a tether, wherein the cover holder removably couples to the cover, the tether couples to the cover holder, and wherein the tether is configured to actuate the switch responsive to the opening in the medicament delivery device being uncovered by the cover.

10. The method of claim 8, further comprising:

generating, with one or more sensors, one or more output signals conveying one or more of information related to one or more parameters of a flow of medicament from the medicament delivery device to the subject, or information related to one or more parameters indicative of usage activity between the subject and the medicament delivery device;

powering the one or more sensors with the power supply responsive to the switch connecting the power supply to the one or more sensors, the switch connecting the power supply to the sensors responsive to the opening in the medicament delivery device being uncovered by the cover; and recording, with the processor, information related to one or more of the one or more parameters of the flow of medicament, or the one or more parameters indicative of usage activity between the subject and the medicament delivery device in the non-transient electronic storage.

11. The method of claim 8, further comprising removably coupling the monitoring system to the medicament delivery device, the coupling performed by the monitoring system, such that the medicament delivery device need not be altered to accommodate the monitoring system.

12. The method of claim 8, wherein the medicament delivery device is one or more of a metered dose inhaler, a pressurized metered dose inhaler, or a dry powder inhaler.

13. A system configured to monitor usage of means for delivering medicament to an airway of a subject, the means for delivering comprising an opening through which medicament is delivered to the subject, the system comprising:

a cover configured to be removably installed at the opening in the means for delivering to cover the opening;

means for powering the system;

means for controlling the system;

means for selectively connecting and disconnecting the means for powering with the means for controlling such that, responsive to the cover being removed from the opening, the means for selectively connecting and disconnecting connects the means for powering with the means for controlling to power up the means for controlling, wherein the cover is releasably connected with the means for selectively connecting and disconnecting and remains connected to the means for selectively connecting and disconnecting even when the cover is disengaged from the opening; and wherein the means for controlling is configured to, responsive to a power up, record information related to the power up to means for non-transient electronic storage, wherein the information related to the power up includes a date and time of powering the means for controlling.

14. The system of claim 13, further comprising means to hold the cover configured to removably couple to the cover, wherein the means to hold the cover is tethered to the means for selectively connecting and disconnecting by the means to tether, wherein the means to tether is configured to actuate the means for selectively connecting and disconnecting responsive to the cover being removed from the opening in the means for delivering.

15. The system of claim 13, further comprising means to generate one or more output signals conveying one or more of information related to one or more parameters of a flow of medicament from the means for delivering to the subject, or information related to one or more parameters indicative of usage activity between the subject and the means for delivering, wherein the means to generate one or more output signals are powered by the means for powering responsive to the means for selectively connecting and disconnecting the means for powering to the means to generate one or more output signals, the means for selectively connecting and disconnecting connects the means for powering to the means to generate one or more output signals responsive to the cover being removed from the opening in the means for delivering, and wherein the means for controlling is configured to cause information related to one or more of the one or more parameters of the flow of medicament, or the one or more parameters indicative of usage activity between the subject and the means for delivering to be recorded to the means for non-transient electronic storage.

16. The system of claim 13, wherein the system is removably coupled to the means for delivering such that the means for delivering need not be altered to accommodate the system.

17. The system of claim 13, wherein the means for delivering is one or more of a metered dose inhaler, a pressurized metered dose inhaler, or a dry powder inhaler.

18. A system configured to monitor usage of a respiratory medicament delivery device, the medicament delivery device configured to deliver medicament to an airway of a subject, the medicament delivery device comprising an opening through which medicament is delivered to the subject and a cover configured to be removably installed at the opening in the medicament delivery device to cover the opening, the system comprising:

a power supply;

a processor; and a switch structured to be connected to the cover via a tether and configured to selectively connect and disconnect the power supply with the processor such that, responsive to the cover being removed from the opening, the switch connects the power supply with the processor to power up the processor, and wherein the processor is configured such that responsive to a power up, the processor causes information related to the power up to be recorded to non-transient electronic storage media.

19. The system of claim 18, further comprising a cover holder configured to removably couple to the cover, wherein the cover holder is connected to the switch by way of the tether, and wherein the tether is configured to actuate the switch responsive to the cover being removed from the opening in the medicament delivery device.

* * * * *